(12) United States Patent
Rajagopalan

(10) Patent No.: US 9,695,199 B1
(45) Date of Patent: Jul. 4, 2017

(54) PENTACYCLIC PYRIDOINDOLOBENZO[B,E]DIAZEPINES AND THIAZEPINES FOR TREATING CNS DISORDERS

(71) Applicant: Daya Drug Discoveries, Inc., St. Peters, MO (US)

(72) Inventor: Parthasarathi Rajagopalan, St. Peters, MO (US)

(73) Assignee: DAYA DRUG DISCOVERIES, INC., St. Peters, MO (US)

( * ) Notice: Subject to any disclaimer, the term of this patent is extended or adjusted under 35 U.S.C. 154(b) by 0 days.

(21) Appl. No.: 15/426,021

(22) Filed: Feb. 6, 2017

Related U.S. Application Data

(63) Continuation-in-part of application No. 14/770,477, filed on Aug. 26, 2015, now Pat. No. 9,598,414.

(51) Int. Cl.
C07D 513/16 (2006.01)
C07D 471/16 (2006.01)
C07D 487/16 (2006.01)

(52) U.S. Cl.
CPC ......... *C07D 513/16* (2013.01); *C07D 471/16* (2013.01); *C07D 487/16* (2013.01)

(58) Field of Classification Search
None
See application file for complete search history.

(56) References Cited

U.S. PATENT DOCUMENTS

2011/0003840 A1*  1/2011  Rajagopalan ........ C07D 498/16
514/280

\* cited by examiner

*Primary Examiner* — Matthew Coughlin
*Assistant Examiner* — Po-Chih Chen
(74) *Attorney, Agent, or Firm* — Raghavan Rajagopalan

(57) ABSTRACT

The present invention discloses pyridoinolobenzo[b,e]diazepine and thiazepine derivatives of Formula 1, Formula I

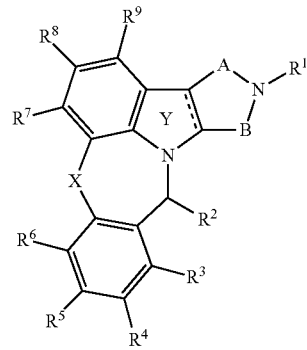

wherein X is $NR^{10}$, S, S(O), or $S(O)_2$. Y is a single bond or no bond. A and B are independently $(CH_2)_m$ and $(CH_2)_n$ respectively; and the subscripts 'm' and 'n' independently vary from 1 to 4. $R^1$ to $R^9$ are various electron donating, electron withdrawing, hydrophilic, or lipophilic groups selected to optimize the physicochemical and biological properties of compounds of Formula I.

27 Claims, 2 Drawing Sheets

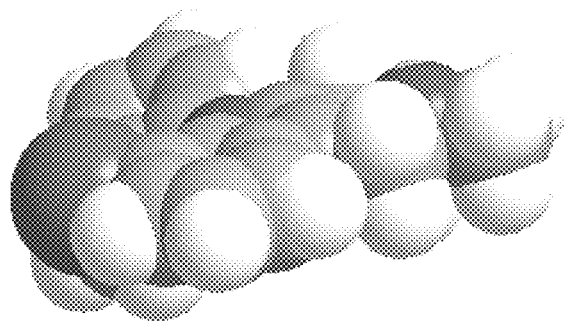
Energy-minimized structure of prior art compound 6b (DDD-016).
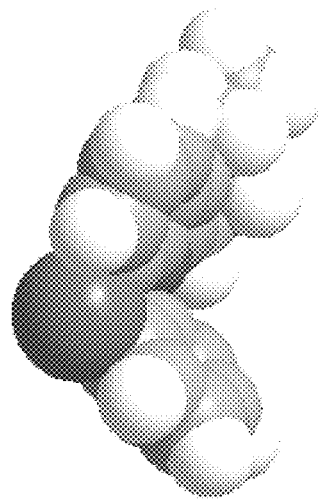
Energy-minimized structure of compound of the present invention (12a).
Figure 1. Energy-Minimized Space-filling models of compounds 6b and 12a.

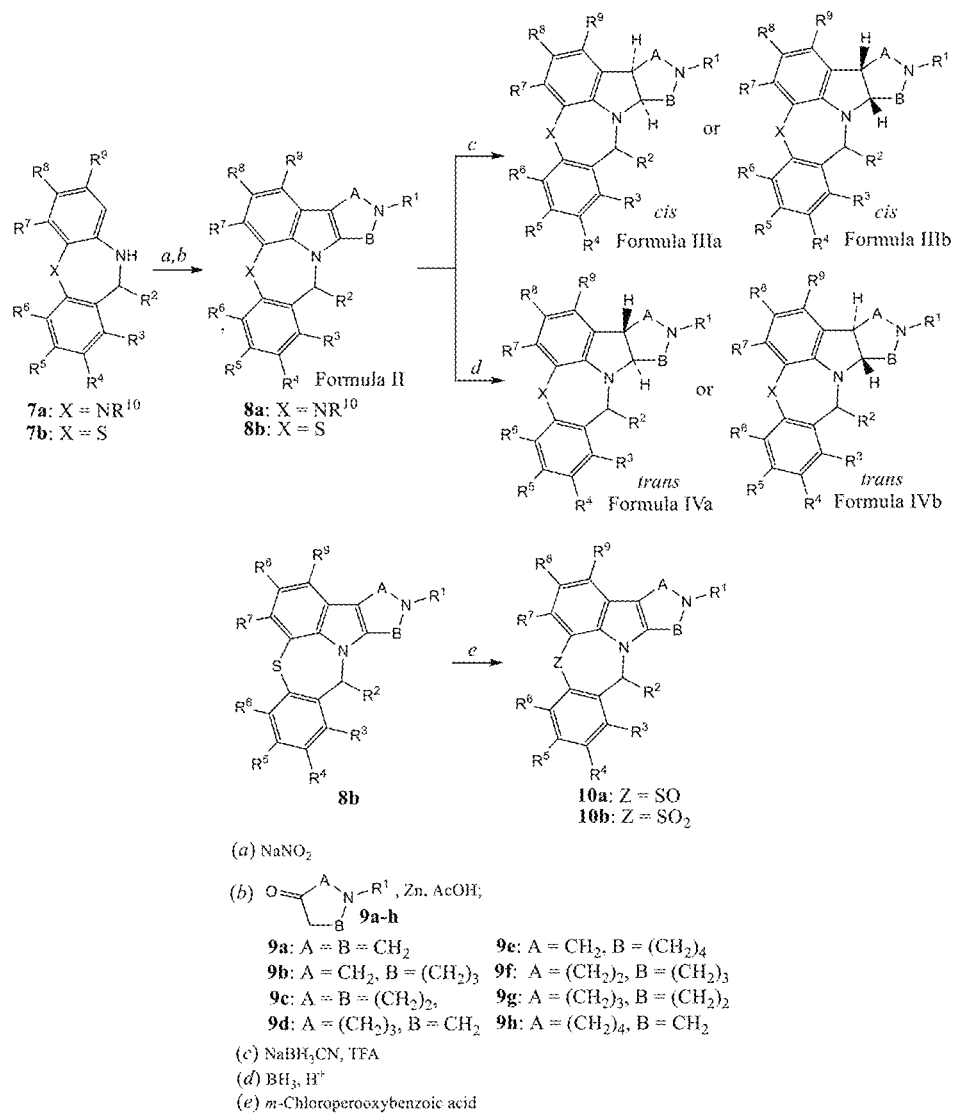
Figure 2. Synthesis of pyridoindolobenzo[b,e]diazepine and thiazepine derivatives.

PENTACYCLIC PYRIDOINDOLOBENZO[B,E]DIAZEPINES AND THIAZEPINES FOR TREATING CNS DISORDERS

CROSS-REFERENCE TO RELATED APPLICATIONS

This application is a continuation-in-part of the previously submitted non-provisional application Ser. No. 14/770,477 filed on Aug. 26, 2015. This application claims benefit of priority based on provisional application No. 61/772,057 filed on Mar. 4, 2013, and said provisional application is incorporated herein by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

This invention relates to novel pentacyclic pyridoindolobenz[b,e]azepine derivatives for the treatment of neurological disorders.

Description of the Related Art

Various prior art references in the specification are indicated by italicized Arabic numerals in brackets. Full citation corresponding to each reference number is listed at the end of the specification, and is herein incorporated by reference in its entirety in order to describe fully and clearly the state of the art to which this invention pertains.

Unless otherwise specified, all technical terms and phrases used herein conform to standard organic and medicinal chemistry nomenclature established by International Union of Pure and Applied Chemistry (IUPAC), the American Chemical Society (ACS), and other international professional societies. The rules of nomenclature are described in various publications, including, "Nomenclature of Organic Compounds," [1], and "Systematic Nomenclature of Organic Chemistry" [2], which are herein incorporated by reference in their entireties.

Neurological disorders comprise several major diseases as described in the Diagnostic and Statistical Manual of Mental Disorders (DSM IV-R) [3]. It is well-established that a particular neurological disorder may involve complex interactions of multiple neuroreceptors and neurotransmitters, and, conversely, a single neuroreceptor may be implicated in several disorders, both neurological and non-neurological. For example, the serotonin receptor is implicated in numerous disorders such as depression, anxiety, pain (both acute and chronic), etc.; the dopamine receptor is implicated in movement disorder, addiction, autism, etc; and the sigma receptors are involved in pain (both acute and chronic), and cancer. Many of the receptors that are found in the brain are also found in other areas of the body, including gastrointestinal (GI) tract, blood vessels, and muscles, and elicit physiological response upon activation by the ligands.

The rational drug design process is based on the well-established fundamental principle that receptors, antibodies, and enzymes are multispecific, i.e., topologically similar molecules will have similar binding affinity to these biomolecules, and, therefore, are expected to elicit similar physiological response as those of native ligands, antigens, or substrates respectively. Although this principle, as well as molecular modeling and quantitative structure activity relationship studies (QSAR), is quite useful for designing molecular scaffolds that target receptors in a "broad sense," they do not provide sufficient guidance for targeting specific receptor subtypes, wherein subtle changes in molecular topology could have substantial impact on receptor binding profile. Moreover, this principle is inadequate for predicting in vivo properties of any compound; hence, each class of compound needs to be evaluated in its own right for receptor subtype affinity and selectivity, and in in vivo models to establish efficacy and toxicity profiles. Thus, there is a sustained need for the discovery and development of new drugs that target neuroreceptor subtypes with high affinity and selectivity in order to improve efficacy and/or minimize undesirable side effects.

Serotonin and sigma receptors are widely distributed throughout the body. To date, fourteen serotonin and two sigma receptor subtypes have been isolated, cloned, and expressed. Serotonin receptors mediate both excitatory and inhibitory neurotransmission, and also modulate the release of many neurotransmitters including dopamine, epinephrine, nor-epinephrine, GABA, glutamate and acetylcholine as well as many hormones such as oxytocin, vasopressin, corticotrophin, and substance P [4, 5]. During the past two decades, serotonin receptor subtype selective compounds have been a rich source of several FDA-approved CNS drugs. Most of these serotonin receptor subtypes have been focus of research in the past couple of decades and this effort has led to the discovery of important therapeutics like Sumatriptan (5-$HT_{1B/1D}$ agonist) for the treatment of migraine, Ondansetron (5-$HT_3$ agonist) for the treatment of radiation or chemotherapy-induced nausea and vomiting, and Zyprexa (5-$HT_{2A}$/$D_2$ antagonist) for the treatment of schizophrenia. Therapeutic targets have been identified for 5-$HT_4$ (learning and memory) [6], 5-$HT_{5A}$ (cognition, sleep) [7], 5-$HT_6$ (learning, memory) [8] and 5-$HT_7$ (pain and depression) [9, 10], and some selective ligands have been prepared for all of these receptors with the exception of 5-$HT_{5A}$. However, no CNS drug has yet emerged out of this effort. Thus, there is a need for selective high affinity agonists and antagonists that target serotonin and dopamine receptors for combating various CNS and peripheral disorders implicated by these neurotransmitter systems.

Among the various CNS disorders, drug addiction continues to be an important target for therapeutic intervention. Drug addiction is a devastating CNS disorder with enormous cost to the individual, family, and society. Presently, there is no cure for drug addiction, and overwhelming majority of patients (nearly 85%) undergoing modern day rehabilitation relapse back into compulsive drug consumption. Relapse is motivated by the intense craving for the drug that is experienced by the drug-withdrawn addict, even after being drug-free for many years. Methamphetamine (meth) (1) and 3,4-methylenedioxyamphetamine (MDMA) (2) are increasingly popular psychostimulant/hallucinogenic drugs with extremely high abuse

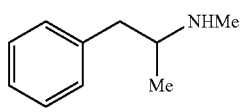
Meth (1)

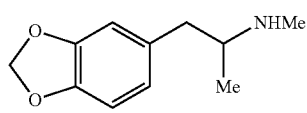
MDMA (2)

liabilities. MDMA, commonly known as 'Ecstasy' is one of the most extensively abused drugs worldwide during the past several years. It is a recreational drug very popular among the 'rave' users and is legally controlled in most countries of the world under UN Convention on Psychiatric Drugs and other international agreements. It is estimated that about 30% of the Americans between the ages of 16 and 25 have used MDMA at least once in their lifetime and majority of them have become habituated to it. The number of life-time users is about 11.6 million in 2009. The cost of treatment meth and MDMA addictions to the individual, society, and the government runs into millions of dollars in the United States alone and, therefore, the development of an effective medication for the treatment of psychostimulant abuse/addiction remains one of the top priorities of the National Institutes on Drug Abuse.

Progress achieved in this field shows the fundamental contribution of brain 5-HT$_{1A}$ and 5-HT$_{2B}$ receptors to virtually all behaviors associated with psychostimulant addiction. Recent data not only show a crucial role of 5-HT$_{1A}$ receptors in the control of brain 5-HT activity and spontaneous behavior, but also their complex role in the regulation of the psychostimulant-induced 5-HT response and subsequent addiction-related behaviors [10] such as comorbid depression. Likewise, Luc Maroteaux et al., reported that serotonin 5-HT$_{2B}$ receptor antagonists are required, and do play an important role in the modulation of serotonin release by MDMA in the brain [11]. These recent findings clearly suggest that 5-HT$_{1A/2B}$ receptor ligands would be useful for the treatment of psychostimulant abuses and comorbidity resulting therefrom.

Rajagopalan [12, 13] and Adams et al. [14] disclosed the pentacyclic scaffolds incorporating the γ-carboline pharmacophore 3-6, where the two phenyl rings are fused at the

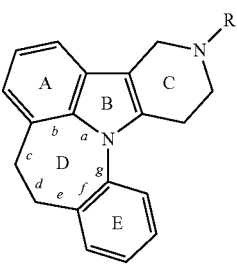
3

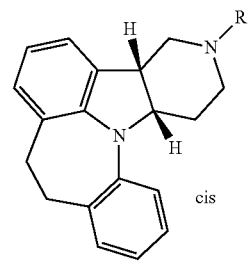
4 cis

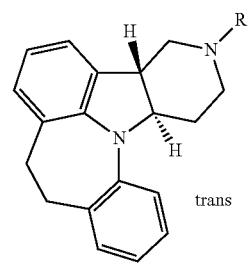
5 trans

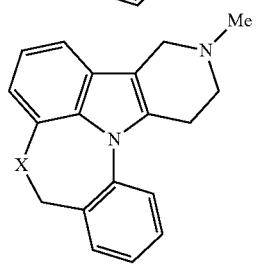
6a: X = CH$_2$
6b: X = S

'b' and 'f' positions in the 7-membered D-ring. In particular, the sulfur analog 6b has been shown recently to have atypical antipsychotic properties [15]. However, other pentacyclic analogs, where the E-phenyl ring being fused at other positions in the 7-membered D-ring, have not been disclosed.

BRIEF SUMMARY OF THE INVENTION

Accordingly, the present invention relates to novel pentacyclic γ-carboline scaffold

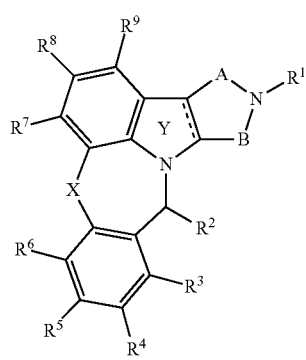
Formula I represented by Formula I, wherein the two phenyl groups are fused at the 'b' and 'e' positions in the 7-membered D-ring.

A and B are independently —(CH$_2$)$_n$—; and 'n' varies from 0 to 3. X is —CHR$^{10}$—; —O—, —NR$^{11}$—, —S—, —SO—, or —SO$_2$—. Y is a single or a double bond. R$^1$ to R$^{11}$ are various electron donating, electron withdrawing, hydrophilic, or lipophilic groups selected to optimize the physicochemical and biological properties of compounds of Formula I. These properties include receptor binding, receptor selectivity, tissue penetration, lipophilicity, toxicity, bioavailability, and pharmacokinetics. Compounds of the present invention are useful for the treatment of neurological disorders, including pain. Moreover, as mentioned before, the receptor binding and pharmacological properties are very sensitive to the overall molecular topology, and these properties cannot be predicted just from the inspection of molecular structure. The overall geometry of the prior art compound 6a is planar whereas the structure of compound 13a of present invention derived from Formula I has a bent conformation with a dihedral angle of about 110° between the E-ring phenyl group and the 7-membered ring as shown in FIG. 1. Hence, the biological activities of the compounds derived from these two scaffolds are expected to be different.

BRIEF DESCRIPTION OF THE SEVERAL VIEWS OF THE DRAWING(S)

FIG. 1. Energy-minimized structures of compounds 6b and 12a.

FIG. 2. General synthetic scheme for pyridoindolobenz[b,e]azepines.

DETAILED DESCRIPTION OF THE INVENTION

The present invention relates to pentacyclic compounds of Formula I, wherein

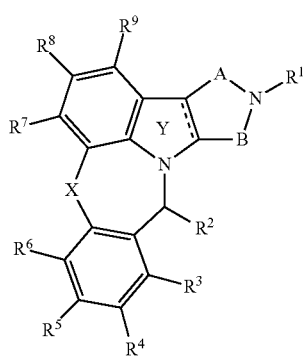

Formula I

X is NR$^{10}$, S, S(O), or S(O)$_2$;
the dotted line, Y, is a single bond or no bond;
A is (CH$_2$)$_m$;
B is (CH$_2$)$_n$; and
subscripts 'm' and 'n' form an ordered pair (m,n), wherein (m,n) is (1,1), (1,2), (2,1), (1,3), (2,2), (3,1), (1,4), (2,3), (3,2), or (4,1);
R$^1$ is selected from the group consisting of hydrogen, C$_1$-C$_{10}$ alkyl, C$_1$-C$_{10}$ hydroxyalkyl, C$_5$-C$_{10}$ aryl unsubstituted or substituted with electron donating groups (EDG) or electron withdrawing groups (EWG), C$_1$-C$_{15}$ aroylalkyl, and C$_1$-C$_{10}$ alkoxycarbonylalkyl, C$_1$-C$_{10}$ carbamoylalkyl, C$_5$-C$_{10}$ arylalkyl unsubstituted or substituted with EDG or EWG;

R$^2$ to R$^9$ are independently selected from the group consisting of hydrogen, C$_1$-C$_{10}$ alkyl, hydroxyl, C$_1$-C$_{10}$ alkoxyl, —NR$^{11}$R$^{12}$, C$_1$-C$_{10}$ hydroxyalkyl, halogen, trihaloalkyl, cyano, carboxyl, C$_1$-C$_{10}$ acyl, C$_1$-C$_{10}$ alkoxyalkyl; C$_1$-C$_{10}$ alkoxycarbonyl; C$_5$-C$_{10}$ aryl unsubstituted or substituted with EDG or EWG, and C$_5$-C$_{10}$ arylalkyl unsubstituted or substituted with EDG or EWG; and R$^{10}$, R$^{11}$, and R$^{12}$ are independently hydrogen or C$_1$-C$_{10}$ alkyl, and R$^{11}$ and R$^{12}$ may optionally be tethered together from a ring.

The phrase, 'electron donating group (EDG)' and 'electron withdrawing group (EWG)' are well understood in the art. EDG comprises alkyl, hydroxyl, alkoxyl, amino, acyloxy, acylamino, mercapto, alkylthio, and the like. EWG comprises halogen, acyl, nitro, cyano, carboxyl, alkoxycarbonyl, and the like.

The first embodiment of the present invention is represented by Formula I, wherein X is NR$^{10}$;

Y is a single bond; and (m,n) is (1,1), (1,2), (2,1), (2,2), or (2,3).

The second embodiment is represented by Formula I, wherein

X is NR$^{10}$;

Y is no bond with cis-fused B|C rings; and (m,n) is (1,1), (1,2), (2,1), (2,2), or (2,3).

The third embodiment is represented by Formula I, wherein

X is NR$^{10}$;

Y is no bond with trans-fused B|C rings; and (m,n) is (1,1), (1,2), (2,1), (2,2), or (2,3).

The fourth embodiment is represented by Formula I, wherein

X is S, SO, or SO$_2$;

Y is a single bond; and (m,n) is (1,1), (1,2), (2,1), (2,2), or (2,3).

The fifth embodiment is represented by Formula I, wherein

X is S, SO, or SO$_2$;

Y is no bond with cis-fused B|C rings; and (m,n) is (1,1), (1,2), (2,1), (2,2), or (2,3).

The sixth embodiment is represented by Formula I, wherein

X is S, SO, or SO$_2$;

Y is no bond with trans-fused B|C rings; and (m,n) is (1,1), (1,2), (2,1), (2,2), or (2,3).

The compounds belonging to Formula I can be synthesized by the well-known Fisher indole condensation of known tricyclic dibenodiazepines 7a and dibenzothiazepines 7b [14, 15] and azacycloalkanones 9a-h as outlined in FIG. 2. Stereospecific reduction of the double

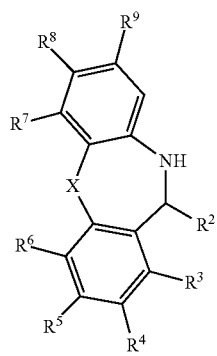

7a: X = NR$^{10}$
7b: X = S

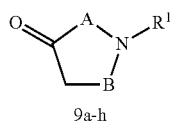

9a-h

9a: A = B = CH$_2$
9b: A = CH$_2$, B = (CH$_2$)$_3$
9c: A = B = (CH$_2$)$_2$
9d: A = (CH$_2$)$_3$, B = CH$_2$
9e: A = CH$_2$, B = (CH$_2$)$_4$
9f: A = (CH$_2$)$_2$, B = (CH$_2$)$_3$
9g: A = (CH$_2$)$_3$, B = (CH$_2$)$_2$
9h: A = (CH$_2$)$_4$, B = CH$_2$ bond in B|C ring junction in formula II (8a or 8b) can be accomplished by NaBH$_3$CN/TFA or with BH$_3$ to give the cis- and trans-reduced compounds of formulas III and IV respectively. Compounds of the present invention may exist as a single stereoisomer or as mixture of enantiomers and diastereomers whenever chiral centers are present. Individual enantiomers can be isolated by resolution methods or by chromatography using chiral columns, and the diastereomers can be separated by standard purification methods such as fractional crystallization or chromatography.

As is well known in the pharmaceutical industry, the compounds of the present invention represented by Formula I, commonly referred to as 'active pharmaceutical ingredient (API)' or 'drug substance', can be prepared as a pharmaceutically acceptable formulation. In particular, the drug substance can be formulated as a salt, ester, or other derivative, and can be formulated with pharmaceutically acceptable buffers, diluents, carriers, adjuvants, preservatives, and excipients. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts include, but are not limited to acetate, adipate, citrate, tartarate, benzoate, phosphate, glutamate, gluconate, fumarate, maleate, succinate, oxalate, chloride, bromide, hydrochloride, sodium, potassium, calcium, magnesium, ammonium, and the like. The formulation technology for manufacture of the drug product is well-known in the art, and are described in "Remington, The Science and Practice of Pharmacy" [16], incorporated herein by reference in its entirety.

The final formulated product, commonly referred to as 'drug product,' may be administered enterally, parenterally, or topically. Enteral route includes oral, rectal, topical, buccal, ophthalmic, and vaginal administration. Parenteral route includes intravenous, intramuscular, intraperitoneal, intrasternal, and subcutaneous injection or infusion. The drug product may be delivered in solid, liquid, or vapor forms, or can be delivered through a catheter for local delivery at a target. Also, it may be administered alone or in combination with other drugs if medically necessary.

Formulations for oral administration include capsules (soft or hard), tablets, pills, powders, and granules. Such formulations may comprise the API along with at least one inert, pharmaceutically acceptable ingredients selected from the following: (a) buffering agents such as sodium citrate or dicalcium phosphate; (b) fillers or extenders such as starches, lactose, sucrose, glucose, mannitol, and silicic acid; (c) binders such as carboxymethylcellulose, alginates, gelatin, polyvinylpyrrolidone, sucrose and acacia; (d) humectants such as glycerol; (e) disintegrating agents such as agar-agar, calcium carbonate, potato or tapioca starch, alginic acid, certain silicates and sodium carbonate; (f) solution retarding agents such as paraffin; (g) absorption accelerators such as quaternary ammonium compounds; (h) wetting agents such as cetyl alcohol and glycerol monostearate; (i) absorbents such as kaolin and bentonite clay and (j) lubricants such as talc, calcium stearate, magnesium stearate, solid polyethylene glycols, sodium lauryl sulfate, and mixtures thereof; (k) coatings and shells such as enteric coatings, flavoring agents, and the like.

Liquid dosage forms for oral administration include pharmaceutically acceptable emulsions, solutions, suspensions, syrups and elixirs. In addition to the API, the liquid dosage forms may contain inert diluents, solubilizing agents, wetting agents, emulsifying and suspending agents, sweetening, flavoring, and perfuming agents used in the art.

Compositions suitable for parenteral injection may comprise physiologically acceptable, sterile aqueous or non-aqueous isotonic solutions, dispersions, suspensions or emulsions, and sterile powders for reconstitution into sterile injectable solutions or dispersions. The compositions may also optionally contain adjuvants such as preserving; wetting; emulsifying; dispensing, and antimicrobial agents. Examples of suitable carriers, diluents, solvents, vehicles, or adjuvants include water; ethanol; polyols such as propyleneglycol, polyethyleneglycol, glycerol, and the like; vegetable oils such as cottonseed, groundnut, corn, germ, olive, castor and sesame oils, and the like; organic esters such as ethyl oleate and suitable mixtures thereof; phenol, parabens, sorbic acid, and the like.

Injectable formulations may also be suspensions that contain suspending agents such as ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the drug in biodegradable polymers. Depending upon the ratio of drug to polymer and the nature of the particular polymer employed, these compositions release the active ingredient(s) only, or preferentially, in a certain part of the intestinal tract, optionally, in a delayed manner. Thus, the rate of drug release and the site of delivery can be controlled. Examples of embedding compositions include, but are not limited to polylactide-polyglycolide poly(orthoesters), and poly(anhydrides), and waxes. The technology pertaining to controlled release formulations are described in "Design of Controlled Release Drug Delivery Systems," [17] incorporated herein by reference in its entirety.

Formulations for topical administration include powders, sprays, ointments and inhalants. These formulations include the API along with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art and are described in "Liposomes," [18], which is incorporated herein by reference in its entirety.

The compounds of the present invention can also be administered to a patient in the form of pharmaceutically acceptable 'prodrugs.' Prodrugs are generally used to enhance the bioavailabilty, solubility, in vivo stability, or any combination thereof of the API. They are typically prepared by linking the API covalently to a biodegradable functional group such as a phosphate that will be cleaved enzymatically or hydrolytically in blood, stomach, or GI tract to release the API. A detailed discussion of the prodrug technology is described in "Prodrugs: Design and Clinical Applications," [19] incorporated herein by reference.

The dosage levels of API in the drug product can be varied so as to achieve the desired therapeutic response for a particular patient. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; activity of the specific compound employed; the specific composition employed, age, body weight, general health, sex, diet of the patient; the time of administration, route of administration, and rate of excretion of the specific compound employed, and the duration of the treatment. The total daily dose of the compounds of this invention administered may range from about 0.0001 to about 1000 mg/kg/day. For purposes of oral administration, more preferable doses can be in the range from about 0.001 to about 5 mg/kg/day. If desired, the effective daily dose can be divided into multiple doses for optimal therapeutic effect.

The following examples illustrate specific embodiments and utilities of the invention, and are not meant to limit the invention. As would be apparent to skilled artisans, various modifications in the composition, operation, and method are possible, and are contemplated herein without departing from the concept and scope of the invention as defined in the claims.

EXAMPLE 1

Proposed Synthesis of Compound of Formula I, Wherein X is $NR^{10}$, Y is a Single Bond, (m,n) is (1,2), $R^1$ and $R^{10}$ are $CH_3$, and $R^2$ to $R^9$ are Hydrogens (11a)

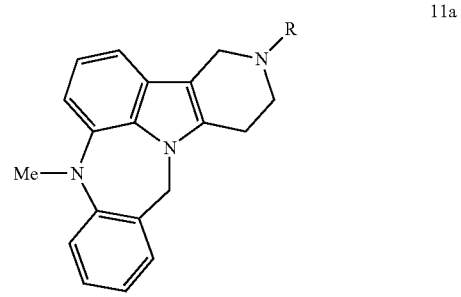

11a

Step 1. 11-Methyl-dibenzo[b,e]diazepine (10 mmol) in ethanol (25 mL), and acetic acid (10 mL) is gently stirred to dissolved all the solids. Thereafter, the solution is cooled to 0° C. in ice bath and treated with a concentrated, aqueous solution of $NaNO_2$ (15 mmol) in water (5 mL) added dropwise over a period of 2-5 minutes. The reaction is stirred at ambient temperature for 1.5 hours and treated with water (30 mL). The crude product is collected by filtration, washed with water, and dried to give the N-nitroso compound. The material is used as such for the next step.

Step 2. A stirring mixture of nitroso compound from Step 1 (1.5 mmol) and 1-methyl-4-piperidone hydrochloride (1.8 mmol) in ethanol (4.5 mL) and acetic acid (1.5 mL) is treated with zinc dust (6.0 mmol) added in three equal portions allowing 5-10 minutes between the additions. The reaction is then stirred at ambient temperature for 2-24 hours. The reaction mixture is cooled to about 0-5° C., and treated with concentrated ammonium hydroxide (5 mL). The reaction mixture is extracted with dichloromethane (3×30 mL). The combined organic layers are washed with brine, dried over anhydrous sodium sulfate, filtered, and the filtrate evaporated in vacuo. The crude material may be used as such for the next step or can be purified by flash chromatography to furnish the hydrazine intermediate.

Step 3. A suspension of the hydrazone from Step 2 (1.3 mmol) in isopropyl alcohol (5 mL) is treated with 2 mL of 2 M solution of hydrogen chloride in dioxane (2.6 mmol), and the entire mixture is heated under reflux for 2 hours. The reaction mixture was cooled to ambient temperature, treated with 10% NaOH (4 mL), and extracted with dichloromethane (3×30 mL). The combined organic layers are washed with brine, dried over anhydrous sodium sulfate, filtered, and the filtrate evaporated in vacuo. The crude product is purified by flash chromatography to obtain the desired product 11a.

EXAMPLE 2

Proposed Synthesis of Compound of Formula I, Wherein X is $NR^{10}$, Y is a Single Bond, (m,n) is (1,1), $R^1$ and $R^{10}$ are $CH_3$, and $R^2$ to $R^9$ are Hydrogens (11b)

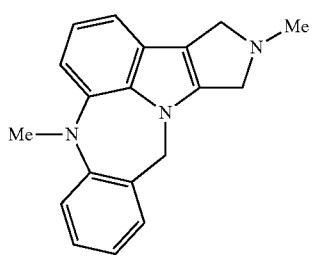

11b

Step 1. The same nitroso compound from Step 1, Example 1 is used herein.

Step 2. The procedure is nearly identical to that of Step 2, Example 1 except that 1-methyl-3-pyrrolidone is used instead of 1-methyl-4-piperidone.

Step 3. The procedure is identical to that of Step 3, Example 1 to give 11b.

EXAMPLE 3

Proposed Synthesis of Compound of Formula I, Wherein X is $NR^{10}$, Y is a Single, (m,n) is (2,2), $R^1$ and $R^{10}$ are $CH_3$, and $R^2$ to $R^9$ are Hydrogens (11c)

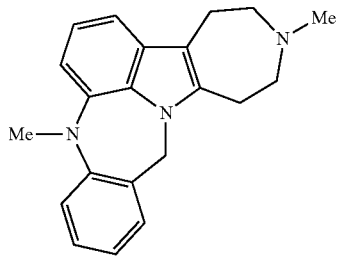

11c

Step 1. The same nitroso compound from Step 1, Example 1 is used herein.

Step 2. The procedure is nearly identical to that of Step 2, Example 1 except that 1-aza-1-methylcycloheptan-4-one is used instead of 1-methyl-4-piperidone.

Step 3. The procedure is identical to that of Step 3, Example 1 to give 11c. Using the same procedure outlined in Steps 1-3 above, other derivatives wherein (m,n) is (1,3) can be prepared by using 1-aza-1-methylcycloheptan-3-one.

EXAMPLE 4

Proposed Synthesis of Compound of Formula I, Wherein X is $NR^{10}$, Y is a Single Bond, (m,n) is (2,3), $R^1$ and $R^{10}$ are $CH_3$, and $R^2$ to $R^9$ are Hydrogens (11d)

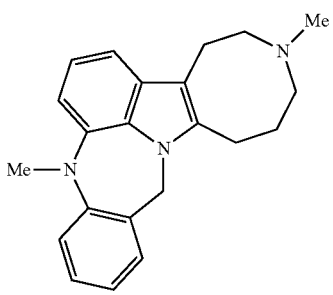

11d

Step 1. The same nitroso compound from Step 1, Example 1 is used herein.

Step 2. The procedure is nearly identical to that of Step 2, Example 1 except that 1-aza-1-methylcyclooctan-5-one is used instead of 1-methyl-4-piperidone.

Step 3. The procedure is identical to that of Step 3, Example 1 to give 11d. Using the same procedure outlined in Steps 1-3 above, other derivatives wherein (m,n) is (1,4) or (2,3) can be prepared by using 1-aza-1-methylcyclooctan-3-one or 1-aza-1-methylcyclooctan-4-one.

EXAMPLE 5

Proposed Synthesis of Compound of Formula I, Wherein X is S, Y is a Single Bond, (m,n) is (1,2), $R^1$ is $CH_3$, and $R^2$ to $R^9$ are Hydrogens (12a)

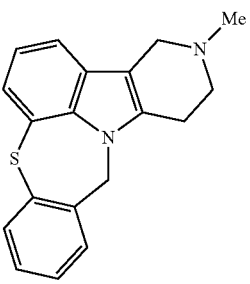

12a

Step 1. Dibenzo[b,e]thiazepine (10 mmol) in ethanol (25 mL), and acetic acid (10 mL) is gently stirred to dissolved all the solids. Thereafter, the solution is cooled to 0° C. in ice bath and treated with a concentrated, aqueous solution of $NaNO_2$ (15 mmol) in water (5 mL) added dropwise over a period of 2-5 minutes. The reaction is stirred at ambient temperature for 1.5 hours and treated with water (30 mL). The crude product is collected by filtration, washed with water, and dried to give the N-nitroso compound. The material is used as such for the next step.

Step 2. A stirring mixture of nitroso compound from Step 1 (1.5 mmol) and 1-methyl-4-piperidone hydrochloride (1.8 mmol) in ethanol (4.5 mL) and acetic acid (1.5 mL) is treated with zinc dust (6.0 mmol) added in three equal portions allowing 5-10 minutes between the additions. The reaction is then stirred at ambient temperature for 2-24 hours. The reaction mixture is cooled to about 0-5° C., and treated with concentrated ammonium hydroxide (5 mL). The reaction mixture is extracted with dichloromethane (3×30 mL). The combined organic layers are washed with brine, dried over anhydrous sodium sulfate, filtered, and the filtrate evaporated in vacuo. The crude material may be used as such for the next step or can be purified by flash chromatography to furnish the hydrazine intermediate.

Step 3. A suspension of the hydrazone from Step 2 (1.3 mmol) in isopropyl alcohol (5 mL) is treated with 2 mL of 2 M solution of hydrogen chloride in dioxane (2.6 mmol), and the entire mixture is heated under reflux for 2 hours. The reaction mixture was cooled to ambient temperature, treated with 10% NaOH (4 mL), and extracted with dichloromethane (3×30 mL). The combined organic layers are washed with brine, dried over anhydrous sodium sulfate, filtered, and the filtrate evaporated in vacuo. The crude product is purified by flash chromatography to obtain the desired product 12a.

EXAMPLE 6

Proposed Synthesis of Compound of Formula I, Wherein X is S, Y is a Single Bond, (m,n) is (1,1), $R^1$ is $CH_3$, and $R^2$ to $R^9$ are Hydrogens (12b)

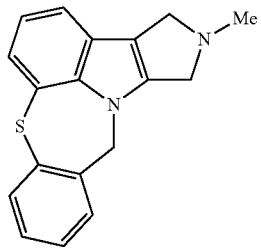

12b

Step 1. The same nitroso compound from Step 1, Example 5 is used herein.
Step 2. The procedure is nearly identical to that of Step 2, Example 5 except that 1-methyl-3-pyrrolidone is used instead of 1-methyl-4-piperidone.
Step 3. The procedure is identical to that of Step 3, Example 5 to give 12b.

EXAMPLE 7

Proposed Synthesis of Compound of Formula I, Wherein X is S, Y is a Single Bond, (m,n) is (2,2), $R^1$ is $CH_3$, and $R^2$ to $R^9$ are Hydrogens (12c)

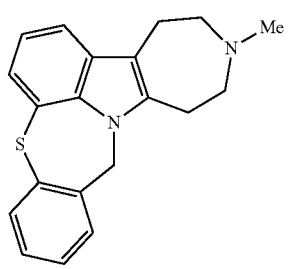

12c

Step 1. The same nitroso compound from Step 1, Example 5 is used herein.
Step 2. The procedure is nearly identical to that of Step 2, Example 5 except that 1-aza-1-methylcycloheptan-4-one is used instead of 1-methyl-4-piperidone.
Step 3. The procedure is identical to that of Step 3, Example 5 to give 12c. Using the same procedure outlined in Steps 1-3 above, other derivatives wherein (m,n) is (1,3) can be prepared by using 1-aza-1-methylcycloheptan-3-one.

EXAMPLE 8

Proposed Synthesis of Compound of Formula I, Wherein X is S, Y is a Single Bond, (m,n) is (2,3), $R^1$ is $CH_3$, and $R^2$ to $R^9$ are Hydrogens (12d)

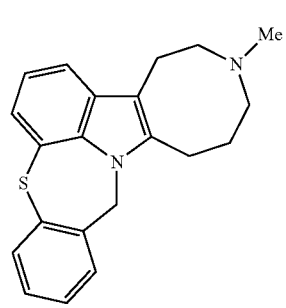

12d

Step 1. The same nitroso compound from Step 1, Example 5 is used herein.
Step 2. The procedure is nearly identical to that of Step 2, Example 5 except that 1-aza-1-methylcyclooctan-5-one is used instead of 1-methyl-4-piperidone.
Step 3. The procedure is identical to that of Step 3, Example 5 to give 12d. Using the same procedure outlined in Steps 1-3 above, other derivatives wherein (m,n) is (1,4) or (2,3) can be prepared by using 1-aza-1-methylcyclooctan-3-one or 1-aza-1-methylcyclooctan-4-one.

EXAMPLE 9

Proposed Synthesis of Compound of Formula I, Wherein X is $SO_2$, Y is a Single Bond, (m,n) is (1,2), $R^1$ is $CH_3$, and $R^2$ to $R^9$ are Hydrogens (12e)

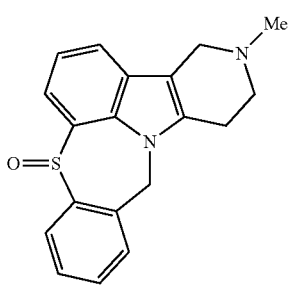

12e

The sulfide 12a from Example 5 (10 mmol) in dichloromethane (15 mL) is treated with a solution of 4-chloroperoxybenzoic acid (MCPBA) (11 mmol) in dichloromethane (15 mL). The reaction is stirred under reflux for 2-8 hours and treated with 1 M NaOH (15 mL). The organic layer is separated, washed with saturated sodium bicarbonate solution (2×20 mL) and water, dried over anhydrous sodium sulfate, filtered, and the filtrate evaporated in vacuo. The crude compound is purified by flash column chromatography to give the sulfone 12e.

EXAMPLE 10

Proposed Synthesis of Compound of Formula I, Wherein X is $SO_2$, Y is a Single Bond, (m,n) is (1,2), $R^1$ is $CH_3$, and $R^2$ to $R^9$ are Hydrogens (12f)

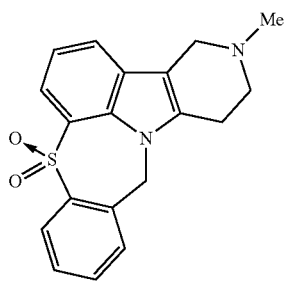

12f

The procedure is identical to Example 9, except that two molar equivalents of MCPBA (22 mmol) is used to give the sulfone 12e

EXAMPLE 11

Proposed General Procedure for the Synthesis of Compound of Formula III, Wherein X is $NR^{10}$ or S, Y is a No with Cis-Fused B|C Rings, (m,n) is (1,2), $R^1$ and $R^{10}$ are $CH_3$, and $R^2$ to $R^9$ are Hydrogens (13, 14)

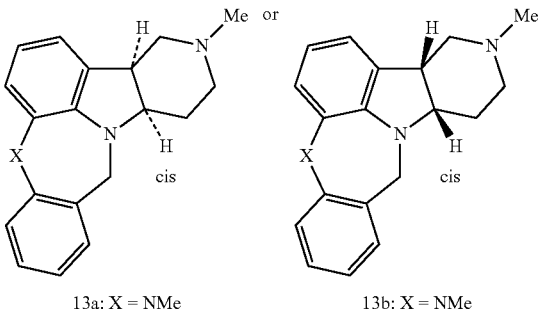

13a: X = NMe  13b: X = NMe
14a: X = S    14b: X = S

A stirred cold solution of compound 11a or 12a from (2 mmol) in trifluoroacetic acid (6.5 mL) at −5° C., is carefully treated with solid sodium cyanoborohydride (2.4 mmol). The reaction mixture is then stirred at ambient temperature for 3 h, treated with 6N HCl solution, and heated under reflux for 30 minutes. The solution is cooled to ambient temperature, and excess trifluoroacetic acid is removed in vacuo. The residue is rendered alkaline with 25% NaOH solution (12 mL), and the solution is extracted with chloroform. The combined organic layers are washed with water and brine, and dried over anhydrous sodium sulfate, filtered, and the filtrate evaporated in vacuo. The crude compound is purified by flash column chromatography to give the enantiomeric mixtures of 13 or 14 respectively. Using the procedure outlined about, all other compounds of formula II can be reduced sterospecifically to the corresponding cis-fused stereoisomers.

EXAMPLE 12

Proposed General Procedure for the Synthesis of Compound of Formula IV, Wherein X is $NR^{10}$ or S, Y is a No with Trans-Fused B|C Rings, (m,n) is (1,2), $R^1$ and $R^{10}$ are $CH_3$, and $R^2$ to $R^9$ are Hydrogens (15, 16)

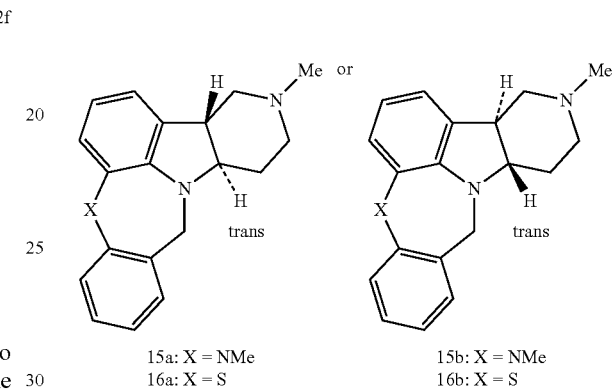

15a: X = NMe  15b: X = NMe
16a: X = S    16b: X = S

The compound 11a or 12a from (1 mmol) is treated with borane-THF (10 mL, 1.0 M) at ambient temperature, and the mixture is heated under reflux for 1 hour. After cooling to ambient temperature, the solution is treated with water to quench excess reagent borane reagent. The solvents are removed under reduced pressure, and the residue is treated with conc. HCl (7 mL). The mixture is heated to reflux for 3 hours and evaporated to dryness in vacuo, and treated with 10% NaOH solution (10 mL). The product is then extracted with ethyl acetate, washed with water and brine, dried over anhydrous sodium sulfate, filtered, and the filtrate evaporated to dryness under reduced pressure. The crude compound is purified by flash column chromatography to give the enantiomeric mixtures of 15 or 16 respectively. Using the procedure outlined about, all other compounds of formula II can be reduced sterospecifically to the corresponding trans-fused stereoisomers.

REFERENCES

1. Fox, R. B.; Powell, W. H. *Nomenclature of Organic Compounds: Principles and Practice*, Second Edition. Oxford University Press, Oxford, 2001.
2. Hellwinkel, D. *Systematic Nomenclature of Organic Chemistry: A Directory of Comprehension and Application of its Basic Principles*. Springer-Verlag, Berlin, 2001.
3. American Psychiatric Association: *Diagnostic and Statistical Manual of Mental Disorders*, 4th Edition. Washington, D.C., Association, A. P., 1994.
4. Roth, B. L. Ed. The Serotonin Receptors. Human Press, Totowa, N.J., 2006.
5. Nichols, D. E.; Nichols, C. D. Serotonin Receptors. *Chem. Rev.* 2008, 108, 1614.
6. Micale, V.; Leggio, G. M.; Mazzola, C.; Drago, F. *Brain Res.* 2006, 112, 207.

7. Jongen-Relo, A. L.; Bespalov, A. Y.; Rueter, L. E.; Freeman, A. S.; Decker, M. W.; Gross, G.; Schoemaker, H.; Sullivan, J. P.; Van Gaalen. M. M.; Wicke, K.; Zhang, M.; Amberg, W.; Garcia-LaDona, *J. Soc. Neurosci. Annual Meet*, Atlanta, Ga. 2006, 526, 29.
8. King, M. V.; Marsden, C. A.; Fone, K. C. A role for the 5-$HT_{1A}$, 5-$HT_4$ and 5-$HT_6$ in learning and memory. *Trends Pharmacol. Sci.* 2008, 29, 482.
9. Brenchat, A. et al. *Pain* 2010, 149, 483-494.
10. Mnie-Filali, O.; Lambas-Senas, L.; Zimmer, L.; Haddjeri, N. *Drug News Perspect.* 2007, 20, 613.
11. Doly, S., Valjent, E., Setola, V., Callebert, J., Herve, D.; Launay, J.-L., and Maroteaux, L. *J. Neurosci.* 2008, 28, 2933.
12. Rajagopalan, P. U.S. Pat. No. 4,438,120; 1984.
13. Rajagopalan, P. U.S. Pat. No. 4,219,550; 1980.
14. Adams, C. W. U.S. Pat. No. 3,983,123; 1976.
15. Bandyopadhyaya, A.; Rajagopalan, D. R.; Rath, N. P., Herrold, A., Rajagopalan, R., Napier, C. T., Tedford, C. E., and Rajagopalan, P. *Medicinal Chemistry Communications* 2012, 3, 580-583.
16. Nandakumar, M. V.; Verkade, J. G. $Pd_2dba_3$/P(i-$BuNCH_2CH_2)_3N$: *Tetrahedron* 2005, 61, 9775-9782.
17. Pharmaceutical Manufacturing. In *Remington: The Science and Practice of Pharmacy*. Lippincott Williams & Wilkins, Philadelphia, 2005, 691-1058.
18. Weissig, V. *Liposomes: Methods and Protocols Volume 1: Pharmaceutical Nanocarriers*. Humana Press, New York, 2009.
19. Li, X. Design of Controlled Release Drug Delivery Systems. McGraw-Hill, New York, 2006.
20. Rautio, J. et al. Prodrugs: Design and Clinical Applications. *Nature Reviews Drug Discovery* 2008, 7, 255.

I claim:

1. A compound of Formula I, wherein

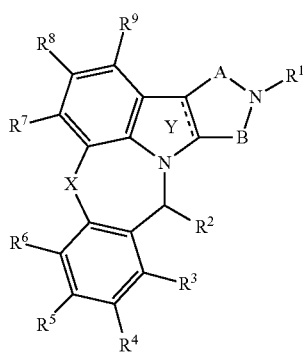

Formula I

X is $NR^{10}$, S, S(O), or $S(O)_2$;
the dotted line, Y, is a single bond or no bond;
A is $(CH_2)_m$;
B is $(CH_2)_n$; and
subscripts 'm' and 'n' form an ordered pair (m,n), wherein (m,n) is (1,1), (1,2), (2,1), (1,3), (2,2), (3,1), (1,4), (2,3), (3,2), or (4,1);
$R^1$ is selected from the group consisting of hydrogen, $C_1$-$C_{10}$ alkyl, $C_1$-$C_{10}$ hydroxyalkyl, $C_1$-$C_{10}$ alkoxycarbonylalkyl, $C_1$-$C_{10}$ carbamoylalkyl, $C_5$-$C_{10}$ aryl, $C_5$-$C_{10}$ arylalkyl, and $C_1$-$C_{15}$ aroylalkyl;
each of $R^2$, $R^3$, $R^4$, $R^5$, $R^6$, $R^7$, $R^8$, and $R^9$ is independently selected from the group consisting of hydrogen, $C_1$-$C_{10}$ alkyl, hydroxy, $C_1$-$C_{10}$ alkoxy, —$NR^{11}R^{12}$, $C_1$-$C_{10}$ hydroxyalkyl, halogen, trihaloalkyl, cyano, carboxy, $C_1$-$C_{10}$ acyl, $C_1$-$C_{10}$ alkoxyalkyl, $C_1$-$C_{10}$ alkoxycarbonyl, $C_5$-$C_{10}$ aryl, and $C_5$-$C_{10}$ arylalkyl; and
each of $R^{10}$, $R^{11}$ and $R^{12}$ is independently hydrogen or $C_1$-$C_{10}$ alkyl.

2. The compound of claim 1, represented by formula II, wherein Y is a single bond:

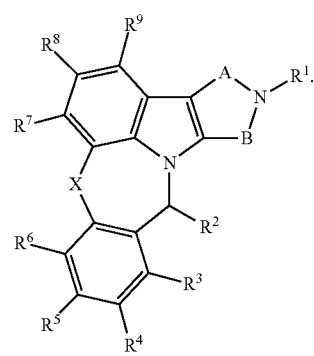

Formula II

3. The compound of claim 2, wherein
X is $NR^{10}$, S; and
$R^2$ is hydrogen.

4. The compound of claim 3, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently selected from the group consisting of hydrogen, $C_1$-$C_{10}$ alkyl, hydroxy, $C_1$-$C_{10}$ alkoxy, and halogen;
each of $R^7$, $R^8$, and $R^9$ is independently hydrogen; and
$R^{10}$ is hydrogen or $C_1$-$C_6$ alkyl.

5. The compound of claim 3, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently hydrogen; and
each of $R^7$, $R^8$, and $R^9$ is independently selected from the group consisting of hydrogen, $C_1$-$C_{10}$ alkyl, hydroxy, $C_1$-$C_{10}$ alkoxy, and halogen.

6. The compound of claim 4, wherein
$R^1$ is hydrogen, $C_1$-$C_{10}$ alkyl, $CH_2Ph$, $CH_2CH_2OH$, or $CH_2CONH_2$; and
each of $R^3$, $R^4$, $R^5$, and $R^6$ is independently hydrogen, $CH_3$, hydroxy, $OCH_3$, F, or Cl.

7. The compound of claim 5, wherein
$R^1$ is hydrogen, $C_1$-$C_{10}$ alkyl, $CH_2Ph$, $CH_2CH_2OH$, or $CH_2CONH_2$; and
each of $R^7$, $R^8$, and $R^9$ is independently hydrogen, $CH_3$, hydroxy, $OCH_3$, F, or Cl.

8. The compound of claim 7, wherein $R^1$ is hydrogen or $CH_3$;
each of $R^7$, $R^8$, and $R^9$ is independently hydrogen; and
$R^{10}$ is hydrogen or methyl.

9. The compound of claim 1, represented by formulas IIIa or IIIb, wherein Y is no bond:

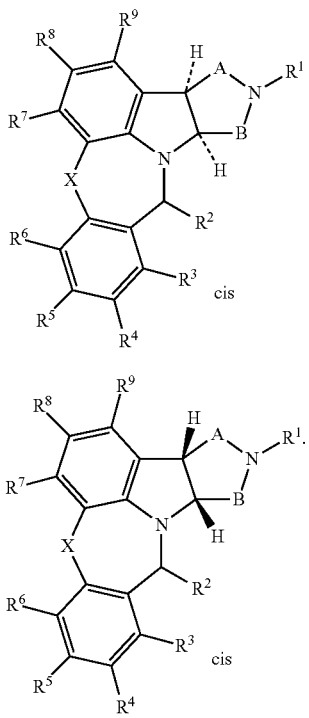

Formula IIIa (cis)

Formula IIIb (cis)

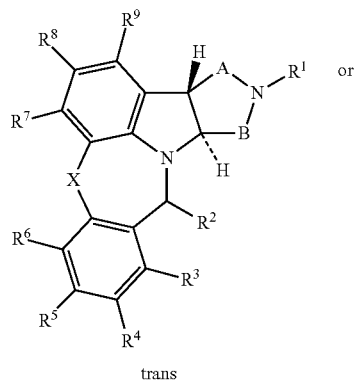

Formula IVa (trans)

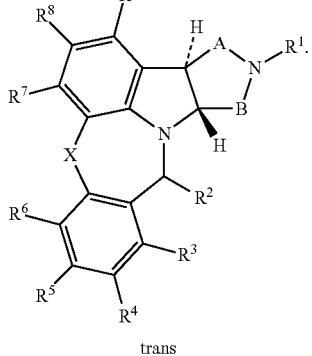

Formula IVb (trans)

10. The compound of claim 9, wherein
X is $NR^{10}$, S; and
$R^2$ is hydrogen.

11. The compound of claim 10, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently selected from the group consisting of hydrogen, $C_1$-$C_{10}$ alkyl, hydroxy, $C_1$-$C_{10}$ alkoxy, and halogen; and
each of $R^7$, $R^8$, and $R^9$ is independently hydrogen.

12. The compound of claim 10, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently hydrogen; and
each of $R^7$, $R^8$, and $R^9$ is independently selected from the group consisting of hydrogen, $C_1$-$C_{10}$ alkyl, hydroxy, $C_1$-$C_{10}$ alkoxy, and halogen.

13. The compound of claim 11, wherein
$R^1$ is hydrogen, $C_1$-$C_{10}$ alkyl, $CH_2Ph$, $CH_2CH_2OH$, or $CH_2CONH_2$; and
each of $R^3$, $R^4$, $R^5$, and $R^6$ is independently hydrogen, $CH_3$, hydroxy, $OCH_3$, F, or Cl.

14. The compound of claim 12, wherein
$R^1$ is hydrogen, $C_1$-$C_{10}$ alkyl, $CH_2Ph$, $CH_2CH_2OH$, or $CH_2CONH_2$; and
each of $R^7$, $R^8$, and $R^9$ is independently hydrogen, $CH_3$, hydroxy, $OCH_3$, F, or Cl.

15. The compound of claim 14, wherein $R^1$ is hydrogen or $CH_3$;
each of $R^7$, $R^8$, and $R^9$ is independently hydrogen; and
$R^{10}$ is hydrogen or methyl.

16. The compound of claim 15, wherein $R^1$ is $CH_3$.

17. The compound of claim 1, represented by formulas IVa or IVb, wherein Y is no bond:

18. The compound of claim 17, wherein
X is $NR^{10}$, S; and
$R^2$ is hydrogen.

19. The compound of claim 18, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently selected from the group consisting of hydrogen, $C_1$-$C_{10}$ alkyl, hydroxy, $C_1$-$C_{10}$ alkoxy, and halogen; and
each of $R^7$, $R^8$, and $R^9$ is independently hydrogen.

20. The compound of claim 18, wherein
$R^1$ is selected from the group consisting of hydrogen, $C_1$-$C_{10}$ alkyl, $C_1$-$C_{10}$ hydroxyalkyl, $C_5$-$C_{10}$ arylalkyl, and $C_1$-$C_{10}$ carbamoylalkyl;
each of $R^3$, $R^4$, $R^5$, and $R^6$ is independently hydrogen; and
each of $R^7$, $R^8$, and $R^9$ is independently selected from the group consisting of hydrogen, $C_1$-$C_{10}$ alkyl, hydroxy, $C_1$-$C_{10}$ alkoxy, and halogen.

21. The compound of claim 19, wherein
$R^1$ is hydrogen, $C_1$-$C_{10}$ alkyl, $CH_2Ph$, $CH_2CH_2OH$, or $CH_2CONH_2$; and
each of $R^3$, $R^4$, $R^5$, and $R^6$ is independently hydrogen, $CH_3$, hydroxy, $OCH_3$, F, or Cl.

22. The compound of claim 20, wherein
$R^1$ is hydrogen, $C_1$-$C_{10}$ alkyl, $CH_2Ph$, $CH_2CH_2OH$, or $CH_2CONH_2$; and
each of $R^7$, $R^8$, and $R^9$ is independently hydrogen, $CH_3$, hydroxy, $OCH_3$, F, or Cl.

23. The compound of claim 22, wherein $R^1$ is hydrogen or $CH_3$; and
each of $R^7$, $R^8$, and $R^9$ is independently hydrogen.

24. The compound of claim 22, wherein $R^1$ is hydrogen or $CH_3$;
   each of $R^7$, $R^8$, and $R^9$ is independently hydrogen; and
   $R^{10}$ is hydrogen or methyl.

25. A pharmaceutical formulation comprising (a) the compound of claim 1 and (b) a pharmaceutically acceptable buffer, diluent, carrier, adjuvant, preservative, or excipient.

26. The pharmaceutical formulation of claim 25, in which the formulation is pharmaceutically acceptable for oral administration.

27. The pharmaceutical formulation of claim 25, in which the formulation is pharmaceutically acceptable for topical administration.

* * * * *